(12) United States Patent
Wakhloo et al.

(10) Patent No.: US 7,185,656 B2
(45) Date of Patent: Mar. 6, 2007

(54) SYSTEM FOR RESTRAINING HEAD AND NECK MOVEMENT

(75) Inventors: Ajay Wakhloo, Miami, FL (US); Marcelo Pizarro, Sherman Oaks, CA (US); Gustavo DeGreiff, Marina Del Rey, CA (US)

(73) Assignee: Ergomd, LLC, Encino, CA (US)

(*) Notice: Subject to any disclaimer, the term of this patent is extended or adjusted under 35 U.S.C. 154(b) by 114 days.

(21) Appl. No.: 11/008,845

(22) Filed: Dec. 9, 2004

(65) Prior Publication Data

US 2006/0124136 A1 Jun. 15, 2006

(51) Int. Cl.
*A69B 19/00* (2006.01)

(52) U.S. Cl. .......................................... 128/869; 5/637

(58) Field of Classification Search ................ 128/845, 128/870, 871, 869; 602/32, 17, 18; 5/637
See application file for complete search history.

(56) References Cited

U.S. PATENT DOCUMENTS 5,147,287 A * 9/1992 Jewell et al. ................. 602/32

\* cited by examiner

*Primary Examiner*—Patricia Bianco
*Assistant Examiner*—Camtu Nguyen
(74) *Attorney, Agent, or Firm*—Dalina Law Group, P.C.

(57) ABSTRACT

The device configured in accordance with one or more embodiments of the invention comprises a base element having a head support region and an upper body support region. The base element is configured to rest upon a base platform that has an attachment point for securing the base element to the base platform and a joint element that enables movement of the base element into an angled position. A restraint mechanism extends from the base platform and is configured to hold the patient's shoulders in position. Head support elements on each side of the device acts as a mechanism for restricting mobility of the patient's head. By holding the shoulders and head the device is able to also restrict neck movement. Reducing patient movement enables diagnostic angiography using a digital subtraction technique (DSA) of the head, neck, and upper shoulder, as well as both non-catheter-based and catheter-based interventions without motion artifact. Restricted movement also provides safe access to the patient for critical procedures which require little or no patient motion while still maintaining a comfortable environment for the patient.

10 Claims, 4 Drawing Sheets

SYSTEM FOR RESTRAINING HEAD AND NECK MOVEMENT

BACKGROUND OF THE INVENTION

1. Field of the Invention

The invention relates to the field of medical devices and is more particularly, but not by way of limitation, directed to an apparatus for supporting and restraining a patient.

2. Description of the Related Art

When doctors and other medical professionals perform certain procedures on a patient, it is sometimes necessary to position the patient in a way that limits patient mobility. For instance, during brain surgery neurosurgeons require the patient's head be immobilized for purposes of performing the surgical operation. In some cases the patient is not sedated during the operation. In such cases not only is immobilization critical, but it is important for the patient to be made as comfortable as possible. Current systems for restraining patient movement exist but these systems lack the usability and functions needed for medical professionals to perform effective operations. For instance, existing systems have problems with blood and saliva contamination (which puts patients at a higher risk of infection) and generally lack mechanism for increasing patient comfort.

For purposes of illustration a brief discussion of several existing systems for restraining patient mobility will now follow. U.S. Pat. No. 6,637,057 describes a head immobilizer that consists of a base headboard for supporting the back of an injured person's head. The base headboard has an elongated slot with teeth racks disposed on either side of the injured person's head. The headboard also comprises straps for attaching to a spine board. Two side head blocks are removably attached to the headboard using plunger-type locks that engage an elongated slot on each side of a center portion of the headboard. Each lock is engaged to a slot of the headboard through a separate elongated slot in the corresponding head block. Advantageously, a head block may be adjusted by moving the engagement of the lock along each independent slot in the headboard and head block, respectively. In addition, a head block may be rotated around its lock. A problem with this head immobilizing system is that it limits access to the patient.

U.S. Pat. No. 5,007,122 describes a head restraint system that utilizes a resilient block of material to wedge a patients head into an state of immobilization. This resilient block has an exterior surface and including a bottom; an inclined front face having a top edge; a rear face; sidewalls; a cavity in the front face forming an interior cavity wall, the intersection of the cavity and the front face having a circumference less than the rear peripheral circumference of the head of a patient; and a split, opening between the cavity and the exterior, intersecting the rear face, the top edge and the front face above the cavity. A problem with this head restraint system is that it provides little room for access to the top of the patient's head during intervention.

U.S. Pat. No. 3,933,154 discloses an immobilizer device that utilizes flexible straps of Velcro™. The immobilizer is used to immobilize a patient during X-ray and surgical procedures. The immobilizer has a back which is adapted to be rigid or bent at various positions. It also has flexible straps for securing different sections of a patient's body against movement in the immobilizer. The immobilizer comprises two parts, a radiotransparent backing member and a radiotransparent flexible part. The backing member is removably inserted under the flexible member with the backing member held firmly by loops and slots on the back of the flexible member. The knee and elbow sections can be produced so as to be used individually and have a unique method of restraining these appendages. The elbow and head restraints are adjustable for patients of different heights. A problem with this immobilizer device retrains the top portion of the head along with the circumference of the head and thereby limits access to that portion of the patient's head during intervention (see e.g., FIG. 4, elements 14 and 19).

U.S. Pat. No. 5,524,639 discloses a jaw support apparatus with supporting arms on each side of a patients jaw and with flexible straps of Velcro. The apparatus is intended to maintain or improve a supine patient's airway in a hands-free environment. A frame and detachable pillow device are placed under the patient's head. Mechanisms extend laterally from the frame and provide jaw support members that may be brought under the angles of the jaw. The jaw support members may slide towards and away from the frame, but this sliding movement is regulated by a unidirectional clutch, such as a ratchet and pawl system, which restricts the jaw support members to sliding movement away from the frame only. When the jaw support members are slid away from the frame, they engage the angles of the jaw, and then thrust the jaw forward to maintain or improve the patient's airway. Once the desired anteriorly thrust position of the jaw is achieved, the unidirectional clutch holds the jaw in place until the clutch is released. The weight of the jaw then causes the jaw support members to slide back towards the frame, restoring the jaw to its normal position. Although the jaw support apparatus retrains the sides of the head, a problem with this jaw support apparatus is that the apparatus limits the amount of accessible area on the sides of the head.

U.S. Pat. No. 5,265,625 a device for immobilizing the head to prevent further injuries such as neck injuries comprises left and right complimentary blocks. Each block has a skull-supporting surface. The blocks contact the skull with the skull supporting surfaces diverging outwardly and upwardly to provide a wedging action to immobilize the skull against left and right movement as well as to position the height of the skull so that alignment of the neck is achieved. The skull supporting surface surrounds but does not cover the ear so that assessment may be made easily. The left and right blocks may be disposable for one time use or permanently mounted on a carrier for reuse. A problem with skull-support apparatus is that the apparatus limits the amount of accessible area on the sides of the head and does not provide a way to incline the patient into a more comfortable position.

Because each of the problems and limitations discussed above exist in these prior art devices there is a need for an apparatus that restrains a patients head while providing adequate support and still allowing access to a patient's head during intervention.

BRIEF SUMMARY OF THE INVENTION

One or more embodiments of the invention are directed to an apparatus for supporting and restraining a patient during a medical procedure, after an accident while being transported, or during other type of intervention. Embodiments of the invention are manifest in various devices for supporting and restraining a patient's head, neck and upper body during various medical procedures or other interventions. A benefit of devices configured in accordance with the invention is that they restrain movement of the head and neck while allowing more access to the head and neck areas than currently available devices.

In one embodiment of the invention various elements of the device rest on a base platform which functions to attach the device with an operating table, stretcher, emergency flat bed or any other surface region for carrying a patient and provides the proper angle of inclination of the head and neck through a hinged attachment to the base element. The base element comprises support regions for the upper body and head. A restraint mechanism extends upwards from the base platform and is configured to hold the patient's shoulders in position. Head support elements on each side of the device act as a mechanism for restricting mobility of the patient's head. By holding the shoulders and head the device is able to also restrict neck movement.

DETAILED DESCRIPTION OF THE INVENTION

Figure 1:
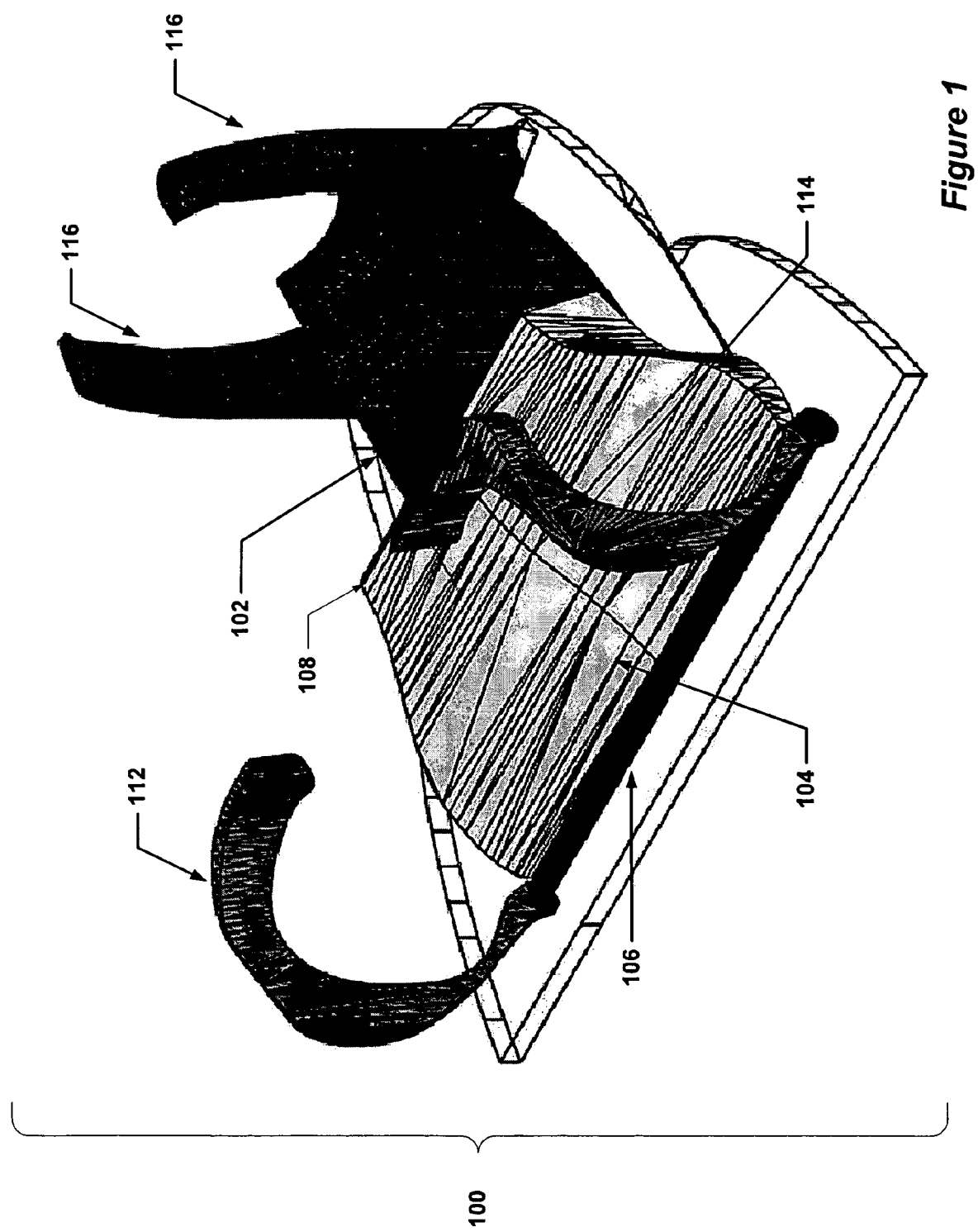
FIG. 1 illustrates a perspective view of an embodiment of the invention.

The following descriptions of the preferred embodiment of the invention are exemplary, rather than limiting, and many variations and modifications are within the scope and spirit of the invention. Although numerous specific details are set forth in order to provide a thorough understanding of the present invention, it will be apparent to one of ordinary skill in the art, that embodiments of the invention may be practiced without these specific details. In other instances, well-known features have not been described in detail in order to avoid unnecessarily obscuring the present invention.

One or more embodiments of the invention are directed to an apparatus for supporting and restraining a patient's head and neck during a medical procedure or other type of intervention. Some examples of the various uses and benefits of the invention are provided below and followed by a description of the structural elements utilized to implement one or more embodiments of the invention.

Exemplary Uses and Benefits of the Invention:

Because the apparatus is configured to provide a stable platform for immobilizing the patient while still enabling access to the patient's head and neck areas the apparatus is able to reduce or eliminate motion that can interfere with procedures performed in the head and neck region or that can prevent further injury during transport of a patient. Such capabilities are beneficial to Interventional Radiologists, Interventional Neuroradiologist, Neurosurgeons, Interventional Cardiologist and in general all physicians who need to restrict the mobility of their patients upper torso, neck and head. For instance, devices configured in accordance with one or more embodiments of the invention enable physician to carry out procedures on patients under conscious sedation or in general anesthesia. Adequate immobilization makes it feasible to utilize cervical spine instrumentation from an anterior approach, perform interventions in the vascular field such as carotid angioplasty, stenting, intracranial angioplasty and stenting, coiling or other endovascular interventions for cerebrovascular diseases but not limited to aneurysm, arteriovenous malformations, dural malformations, fibrinolysis for acute ischemic stroke, and thrombectomy.

The apparatus also has applicability in other areas where patient stability is required. For instance, the device us useful when performing biopsies for tumors in head and neck area, vertebroplasty of the cervical spine, kyphoplasty, or other procedures where immobilization of the patient while maintaining access to the head and neck region is desired. The restraining apparatus is also useful for interventions in the upper shoulder regions as it is possible to use the upwardly extending arms coupled to the device to stabilize this area of the patient. Some examples of other interventions the apparatus is capable of assisting include, but are not limited to, procedures relating to the subclavian venous and arterial systems, biopsies of soft tissues for obtaining specimen for histology or direct puncture of vascular and tumor lesions to apply drug treatment or tumor therapy, such as radiofrequency ablation. The restraining apparatus is also useful for transport of injured victims where head, neck and upper body immobilization is critical to prevent further injury.

Benefits provided when using one or more of the embodiments of the invention may include, but are not limited to, enabling easy access to the endo-nasal or oral regions of the patient. Moreover, the apparatus does not interfere with the application of general anesthesia and provides access to the patient for purposes ventilation or for whatever other reason is required. Because the device provides users with the ability to easily elevate the patient, it is possible during procedures where it may be necessary to lightly sedate the patient (e.g., in neurosurgical uses) for physicians to engage in a dialog with the patient while in the midst of a procedure. The ability to have conversations with the patient is generally required for all interventions performed on patients under conscious sedation. The device can also be used to immobilize the head and neck area of patients with ischemic stroke who undergo angiography on the angiographic unit, in CT, or in MR and are not cooperative, but cannot be sedated because of the need for neurological monitoring. Another possible use for the device as described herein is to immobilize patients with cervical trauma for purposes of transport or to perform a particular procedure.

Other benefits of using the device described herein include:

Eliminating the need to reposition non-cooperative patients

Providing different degrees of ante- and retroflection of the head

Stabilization of head and neck in various angles in ante- and retroflexion

The use of non-radio-opaque materials for digital subtracted angiography and standard conventional angiography.

No interference with X-ray beam for fluoroscopy, neither in anterior-posterior or lateral or any other projections.

Non-ferromagnetic materials with no interference with Magnetic Resonance imaging/system Simple open system that prevents claustrophobia.

The need for an open system which allows verbal and non-verbal communication between the physician, the nursing staff, the x-ray technologist, and the patient Comfort to the patient Can be installed with ease to all known medical and surgical tables.

Hygienic One-time use

Ease of attachment to surgical and angiographic tables

Repels fluids such as but not restricted to saline and blood

The structural elements of the device providing these and other benefits is described in detail below.

Structural Elements of the Invention:

Devices configured in accordance with one or more embodiments of the invention comprises a base element having a head support region and an upper body support region. The base element is configured to rest upon a base platform that has one or more attachment points for securing the base element to the base platform and a joint element that enables movement of the base platform and hence the base element into an inclined position. A restraint mechanism extends upwards from the base platform and is configured to hold the patient's shoulders in position. Head support elements on each side of the device act as a mechanism for restricting mobility of the patient's head. By holding the shoulders and head the device is able to also restrict neck movement. It is the devices ability to reduce patient movement while leaving open access to the head and neck areas of the patient that enables users to perform procedures such as a diagnostic angiography using a digital subtraction technique (DSA) of the head, neck, and upper shoulder, as well as both non-catheter-based and catheter-based interventions. Restricted movement also provides safe access to the patient for any procedure requiring little or no patient motion while still maintaining a comfortable environment for the patient.

It is feasible to use various materials for the various elements of the invention. The base elements generally use pliable materials that are likely to provide effective patient comfort (e.g., foam, fabric, plastic, elastomeric, or other plastic type materials). However, it is feasible to use other and more rigid materials while still staying within the scope and spirit of the invention. Elements of the apparatus described herein that must have the ability to withstand frequent use are typically made with a metal or rigid plastic or plastic type materials, but can also be designed using any material that tolerates fairly regular use. In a disposable embodiment of the invention the ability to tolerate such use is unnecessary and devices may then utilize inexpensive materials to provide a low cost device that be readily disposed. A benefit of the disposable embodiment of the invention is that it provides for hygienic one time usage and thereby provides patients with added comfort as to the cleanliness of the procedure.

FIG. 1 illustrates an embodiment of the invention configured to support a patient's neck and head region while still providing access to the patient for purposes of performing various types of procedures. The device illustrated in FIG. 1 contains a base element 100 contoured to support a patient's upper back, neck, and head. Base element 100 comprises one or more ergonomically shaped segments (e.g., a head support region and upper body support region). Each of these shaped segments can take any form fitting shape and are typically configured to give the patient optimum comfort while in a reclined position. For instance, the portion of the base element upon which the patient's head rests (referred to as head support region 102) is generally curved inward like the inner surface of a bowl or sphere. Hence this head support region 102 limits head mobility while increasing patient comfort. It is possible for head support region 102 to take any inwardly curved shape and although a variety of inwardly curved shapes are sufficient for purposes of increasing patient comfort, in one or more embodiments of the invention head support region 102 is concaved to a depth sufficient to limit head movement while still maintaining patient comfort.

In addition to head support region 102 having a generally concave form one or more embodiments of the invention include a set of one or more head support elements 116. These head support elements 116 extend from head support region 102, a base platform, or any other region within reasonable proximity to head support region 102 and are configured to restrict mobility of the patient's head. In one embodiment of the invention head support elements 116 are positioned on each side of head support region 102 and generally shaped to fit the contours of the patient's head. By surrounding portions of the patient's head region head support elements provide an additional mechanism for limiting patient movement.

In one embodiment of the invention head support region 102 is given a deep enough concave to limit patient movement without the use of head support elements 116. When head elements are not present an end of head support region 102 is left open to allow unencumbered access to the patient's head. In this case head support region 102 takes the form of a bowl having a side cut off. Even when the end of head support region 102 is left open head support elements 116 can be optionally included to limit side-to-side movement of the patient's head.

Disposed adjacent to or coupled with head support region 102 is an upper body support region 104. Upper body support region is ergonomically shaped to provide support to the patient's upper back and shoulder area. For instance, one embodiment of the invention provides an upper body support region 104 that has a lower side 106, an upper side 108 and a top region 107 that inclines from lower side 106 to upper side 108. A base region 109 of upper body support region 104 couples with a base platform that acts as a support mechanism for both body support region 104 and head support region 102. Although elements may intervene between body support region 104 and head support region 102 body support region 104 typically adjoined to or abuts with head support region 102 thereby making a uniform support for the patient's upper chest, neck and head areas.

Devices configured in accordance with one or more embodiments of the invention may utilize an additional element intended to limit movement of the patient's upper chest region and referred to herein as restraint mechanism 110. Although restraint mechanism 110 can take various forms, it at least one instance restraint mechanism comprises a set of one or more upwardly extending arms (e.g., arms 112 and 114). These upwardly extending arms couple with a base or optionally a joint that allows for upward and/or lateral movement of arms 112 and 114. When a joint is used, the joint is affixedly coupled with a base platform, body support region 104 or any other structural element able to support arms 112 and 114 and within reasonable proximity to the patient's upper chest area (e.g., a hospital bed, surgical table, etc . . . ).

Figure 2:
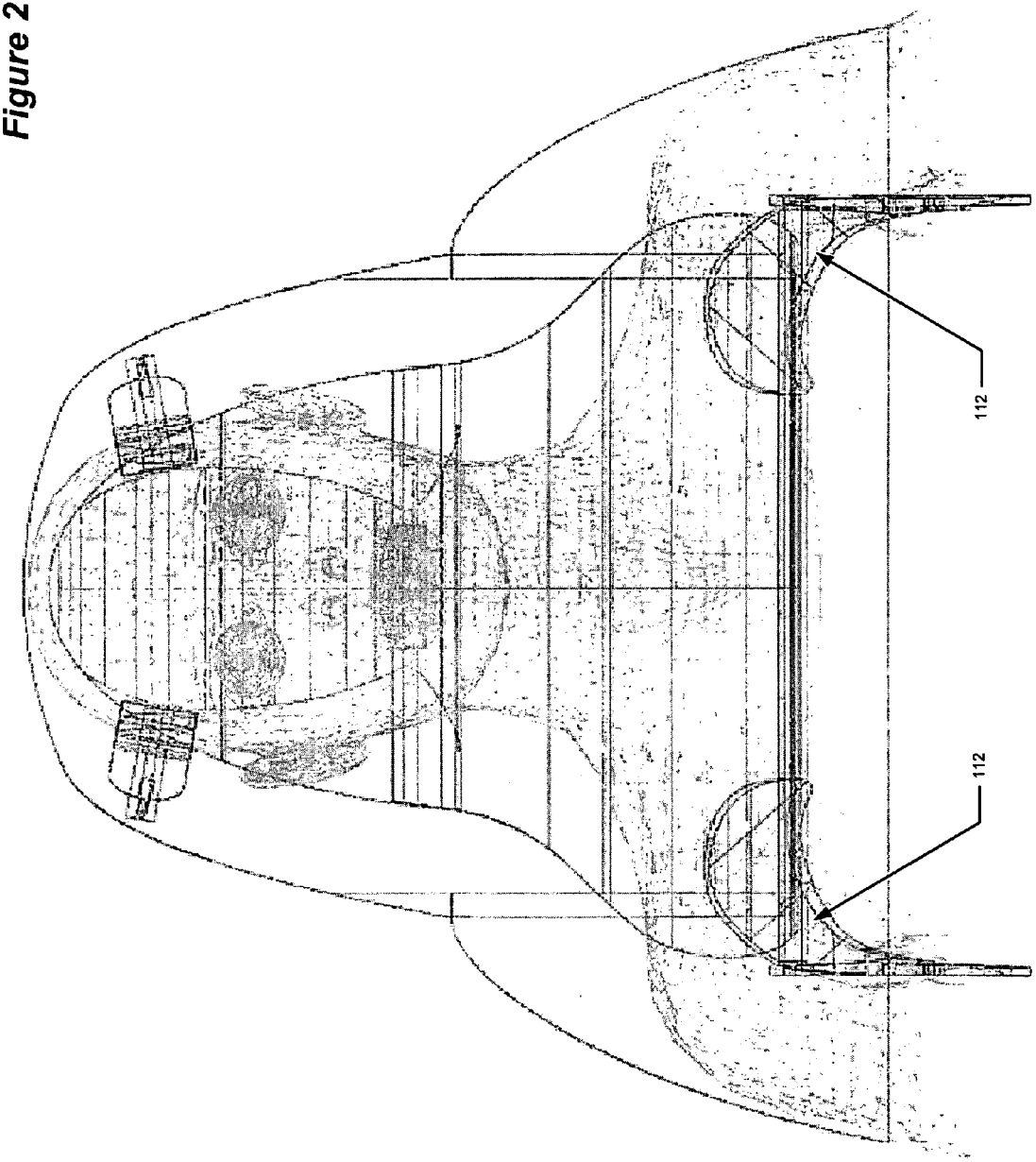
FIG. 2 illustrates a top view of an embodiment of the invention and shows an example positioning of the extended support arms.

Upwardly extending arms 112 and 114 can take various forms but are generally shaped to surround parts of the patient's chest region. For instance, in at least one case arms 112 and 114 shaped to extend from a base or joint proximate to a patient's arms and around the patient's chest or shoulder area. FIGS. 1 and 2 depict the placement of this underarm configuration in accordance with one or more embodiments of the invention, however other configurations that generally extend across the patient's upper chest and/or shoulder area are also within the scope of the invention. Embodiments of the invention other than the ones depicted here may contain restraint mechanisms that utilize a single arm or multiple arms that wrap around the patient's chest region in order to hold the patient in an immobilized position.

In one or more embodiments of the invention arms 112 and 114 it is possible to adjust the distance between arms 112 and 114 to make the device comfortable for patients of varying size. In such cases the point where arms 112 and 114 anchor to the base (e.g., a base or joint) is coupled with an adjustable element that allows for the extension and retraction of arms 112 and 114. In some instances one or more the upwardly extending arms are coupled with a joint mechanism that allows for lateral, vertical or any other directional movement necessary to enable the patient to comfortably access the apparatus. Hence joint element may utilize hinges single directional, swivel, ball joints, or any other mechanism that allows for movement of restraint arm 112 around the patient. When the system utilizes a ball joint with a locking mechanism it is feasible to move the restraint arm into numerous positions as may be required by a particular patient.

Figure 3:
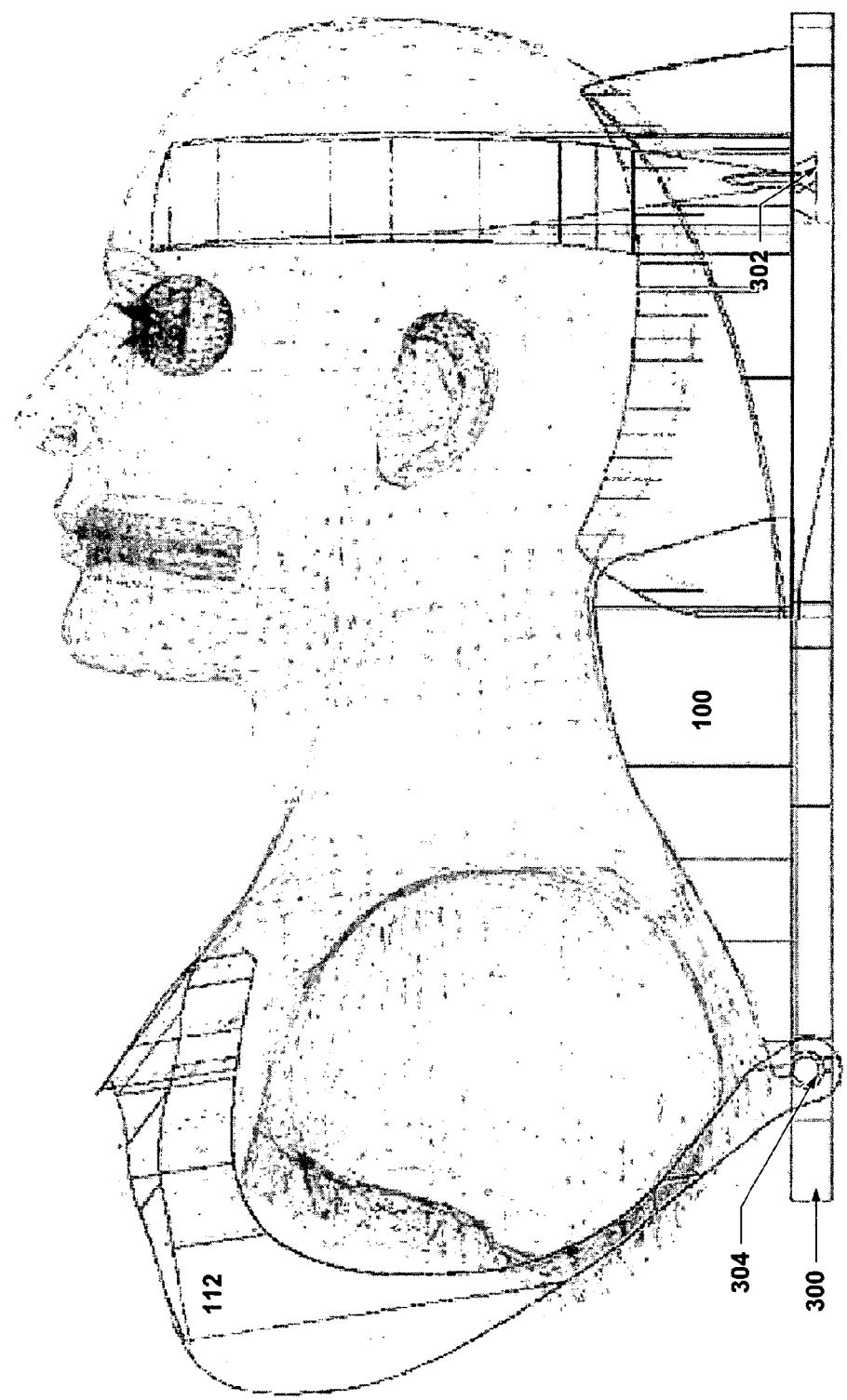
FIG. 3 illustrates a side view of an embodiment of the invention and shows an example location for an attachment point to secure the base element.

In one or more embodiments of the invention base element 100 (e.g., head support region and upper body support region) rests upon or is coupled with a base platform. FIG. 3 illustrates base platform 300 with base element 100 attached at attachment point 302. Although attachment point 302 is used herein for purposes of illustration one of skill in the art will recognize that various points of attachment are suitable for purposes of limiting slippage of base element 100. It is also feasible to configure base element 100 to interlock with base platform in a way that limits slippage, but does not require use of an attachment point.

Figure 4:
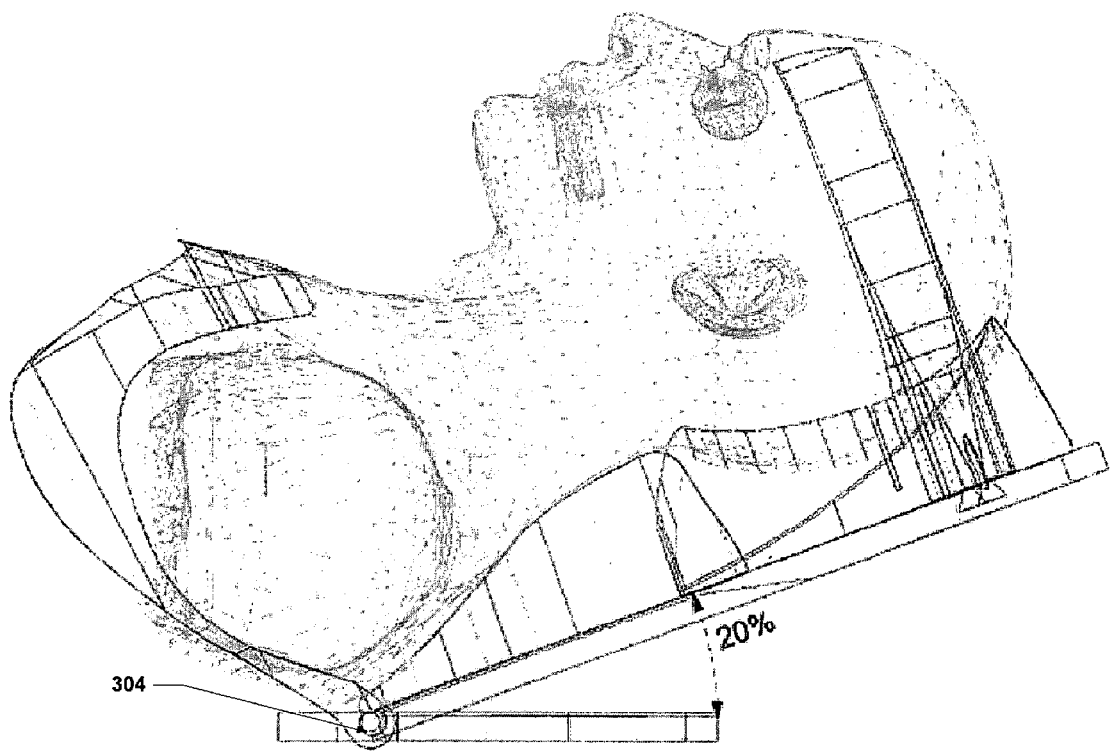
FIG. 4 illustrates a side view of an embodiment of the invention and shows how the base element can be inclined.

Referring still to FIG. 3, an example of joint 304 is illustrated. Joint element 304 provides a mechanism for pivoting base element 100 (and thereby the patient's head and chest region) into an inclined position of varying degree as depicted in FIG. 4. Having the ability to move the patient into positions that elevate the head and upper chest region of the patient increase patient comfort and can improve the ease with which access to the patients neck or head region can be obtained. Such functionality is particularly useful for patients with cervical degenerative changes and idiopathic diseases such as Diffuse Idiopathic Skeletal Hyperostosis (DISH) which prevent a proper supine horizontal positioning of the patient. It is possible to utilize various mechanisms to provide movement of base element 100 and hence it is within the scope a spirit of the invention to utilize any mechanical element that allows for movement of base element 100. Embodiments of the invention may also utilize a joint element that contains a locking mechanism able to lock said base element in said inclined position. The joints described herein may be mechanical, hydraulic, or motorized.

Thus an example of an apparatus for restraining and supporting a patient's head as well as potential methods of use has been described. The claims however, and the full scope of their equivalents are what define boundaries of the invention.

What is claimed is:

1. An apparatus for restraining and supporting a patient comprising:
    a base element having a head support region and an upper body support region;
    said head support region comprising an inwardly shaped surface and a base surface where said inwardly shaped surface is concaved to act as a head rest for a patient sitting in a reclined position for purposes of receiving a procedure to be administered;
    said upper body support region comprising a base surface, a lower side and a higher side and having a surface region that inclines from said lower side to said higher side and is contoured to provide a comfortable place for the patient's shoulders and upper chest area and neck to rest;
    a set of one or more upwardly extending arms where said set of upwardly extending arms are configured to wrap around said patient's upper body area and coupled with a base platform wherein said set of upwardly extending arms are shaped to extend from said base platform under a patient's arm and across said patient's chest region; and
    said base platform coupled with said base surface of said head support region and said upper body support region and having a joint element configured to enable movement of said base element into a inclined position.

2. The apparatus of claim 1 wherein said joint element comprises a locking mechanism configured to enable locking of said base element in said inclined position.

3. The apparatus of claim 1 wherein said base platform is coupled with said base support surface via an attachment point.

4. The apparatus of claim 1 further comprising a set of one or more head support elements coupled with said base platform and configured to restrict movement of a patient's head.

5. The apparatus of claim 1 wherein said set of upwardly extending arms comprises a pair of upwardly extending arms and further comprising a extension mechanism for changing the distance between said pair to accommodate said patient.

6. The apparatus of claim 1 wherein said set of upwardly extending arms are coupled with a joint element configured to enable movement of said arms.

7. The apparatus of claim 1 wherein said base platform is coupled with a hospital bed.

8. The apparatus of claim 1 wherein said joint element comprises a motorized mechanism.

9. An apparatus for restraining and supporting a patient comprising:
    a base element having a head support region and an upper body support region;
    said head support region comprising an inwardly shaped surface and a base surface where said inwardly shaped surface is concaved to act as a head rest for a patient sitting in a reclined position for purposes of receiving a procedure to be administered;
    said upper body support region comprising a base surface, a lower side and a higher side and having a surface region that inclines from said lower side to said higher side and is contoured to provide a comfortable place for the patient's shoulders and upper chest area and neck to rest;
    a set of one or more upwardly extending arms where said set of upwardly extending arms are configured to wrap around said patient's upper body area and coupled with a base platform wherein said set of upwardly extending arms are shaped to extend from said base platform under a patient's arm and across said patient's chest region;

said base platform coupled with said base surface of said head support region and said upper body support region and having a joint element configured to enable movement of said base element into a inclined position; and, a set of one or more head support elements attached with said base platform and configured to restrict movement of a patient's head.

10. The apparatus of claim 9 wherein said set of one or more head support elements are configured to restrict the rotation of said patient's head about an axis parallel to said patient's spine.

* * * * *